United States Patent [19]

Schürle et al.

[11] Patent Number: 5,331,358
[45] Date of Patent: Jul. 19, 1994

[54] VISION TESTING SYSTEM FOR TESTING THE SIGHT FUNCTION OF A PATIENT

[75] Inventors: Hermann Schürle, Aalen; Wolfgang Grimm, Heidenheim; Hartmut Mennicke, Pullach, all of Fed. Rep. of Germany

[73] Assignee: Carl-Zeiss-Stiftung, Heidenheim/Brenz, Fed. Rep. of Germany

[21] Appl. No.: 879,995

[22] Filed: May 8, 1992

[30] Foreign Application Priority Data

May 8, 1991 [DE] Fed. Rep. of Germany ....... 4115145

[51] Int. Cl.⁵ .................. A61B 3/02; G02B 27/02; H04N 13/00
[52] U.S. Cl. .................. 351/232; 351/201; 351/240; 359/464; 348/58
[58] Field of Search ............... 351/201, 203, 232, 239, 351/240, 243, 233, 246; 359/464, 465; 358/3, 88, 91, 92

[56] References Cited

U.S. PATENT DOCUMENTS

| | | | |
|---|---|---|---|
| 3,191,493 | 6/1965 | Mainardi et al. | 359/465 |
| 4,097,130 | 6/1978 | Cole | |
| 4,415,243 | 11/1983 | Gottlob et al. | 351/201 |
| 4,792,850 | 12/1988 | Lipton et al. | 358/88 |
| 4,870,486 | 9/1989 | Nakagawa et al. | 358/92 |
| 4,877,309 | 10/1989 | Takamatsu | |
| 5,026,151 | 6/1991 | Waltuck et al. | 351/246 |

FOREIGN PATENT DOCUMENTS

| | | |
|---|---|---|
| 0060986 | 9/1984 | European Pat. Off. |
| 0274391 | 7/1988 | European Pat. Off. |
| 3043511 | 6/1982 | Fed. Rep. of Germany |
| 60-216337 | 10/1985 | Japan |
| 63-274918 | 11/1988 | Japan ................................. 359/464 |

OTHER PUBLICATIONS

"Stereoscopic Display Techniques Improve 3-D Workstation Views" by D. Brokenshire et al, Computer Technology Review, vol. 8, No. 13, 1988.

Primary Examiner—Loha Ben
Assistant Examiner—Michael A. Papalas
Attorney, Agent, or Firm—Walter Ottesen

[57] ABSTRACT

A vision testing system includes polarization spectacles having different polarization axes with or without λ/4 filters for the two polarization lenses forward of the eye of the patient to be tested. This system also includes a vision testing apparatus for generating light having a specific polarization direction. The vision testing apparatus includes essentially two polarization filters and two LCD-displays which are mounted alternately one behind the other. This arrangement can so influence the light coming from the light source that test figures or portions of the test figures can be seen by one eye or by both eyes. If a test figure is to be changed, then a corresponding command is issued via a key pad to a switching unit which drives two drive circuits of the two LCD-displays in a desired manner. By making appropriate modifications of the vision testing apparatus, a patient can be tested as to color-vision acuity.

9 Claims, 5 Drawing Sheets

VISION TESTING SYSTEM FOR TESTING THE SIGHT FUNCTION OF A PATIENT

FIELD OF THE INVENTION

The invention relates to a vision testing system for testing the vision functions of a patient wherein the light emitted by a vision testing apparatus has a polarization direction defined for a region and which has polarization spectacles for the eyes of the patient to be tested. The polarization lenses of the spectacles have a first polarization axis for the one eye and a second polarization axis for the other eye of the patient with the second polarization axis being perpendicular to the first polarization axis. The polarization lenses permit the light emitted by the vision testing apparatus to be seen only in certain regions.

BACKGROUND OF THE INVENTION

Optical test charts and vision testing devices are disclosed, for example, in U.S. Pat. No. 4,415,243 with which a patient is tested for the monocular and binocular vision functions. This check is performed in that the patient looks through a polarization filter in front of each eye at illuminated plates with the polarization filters having mutually crossed directions of oscillation. These plates have regions with different polarization actions so that the patient can recognize different regions with both eyes. The optical test charts have the disadvantage that the intensity of the luminosity is dependent upon the ambient luminosity and that, for each test, a plate must be moved manually. Vision testing devices avoid this disadvantage since the plates therein are illuminated from behind and a switchover to another test takes place by remote control with a plate exchange taking place mechanically in the apparatus. The known optical test charts and vision testing apparatus have the common disadvantage that the plates cannot be changed by the person conducting the test without considerable difficulty since the production of the plates is very time intensive.

U.S. Pat. No. 4,870,486 discloses a virtual stereographic image display system wherein a polarizer and a liquid-crystal cell are mounted forward of an image-display surface of a TV-monitor. The light emanating from this image-display system is viewed by a viewer through polarization spectacles with the individual lenses of the spectacles having different polarization axes. This image-display system requires a large space because of the monitor and simply serves to generate virtual stereoscopic images.

A color liquid-crystal image-generating arrangement is disclosed in U.S. Pat. No. 4,877,309 which operates with two liquid-crystal image-generating cells. Two color polarizers are disposed in front of these two image-generating cells and, in addition, a neutral polarizer is disposed at the light-incident side of the first image-generating cell.

This color liquid-crystal image-generating arrangement generates only color images and, taken by itself, is unsuitable for a vision testing system for testing the binocular vision functions.

Published German patent application 3,043,511 discloses an arrangement for testing the function of the eye and of the vision system. The visual display takes place by means of monitors and is for the binocular testing with two monitors having polarizers or with one monitor (red-green stereopsis). This arrangement requires a large space and is usable only in a limited manner for vision testing when using only one monitor.

SUMMARY OF THE INVENTION

It is an object of the invention to provide a compact vision testing system wherein the testing of the vision functions is made possible with test figures easily changeable and simultaneously displayed.

The vision testing system of the invention is very flexible with respect to its use notwithstanding the compactness thereof. If other characters are to be shown for vision testing, then this can inputted very rapidly into the computer via the key pad. By driving the drive circuit of the two LCD-displays (LCD I and LCD II), which are mounted one behind the other, the computer ensures that the desired image appears on the vision testing system. The illumination in the vision testing system can be provided by one or several light sources. The regions of the two LCD-displays are each driven individually and must be so aligned to each other that the region boundaries are coincident. Furthermore, the regions must be adapted to each other with respect to their sizes. This does not mean that they must be the same size. It is also conceivable that the LCD-displays have liquid-crystal cells of different size which are drivable in a discrete manner. The LCD-display with the lower resolution (that is, a lower number of discretely drivable regions) then determines the smallest displayable characters or regions.

Active-matrix displays in TN-technology are advantageously used for the vision testing system. These active-matrix displays are characterized by a polarization response which is dependent only slightly on the Wavelength of the light used. Furthermore, cross talk from driven image points to non-driven image points, which occurs with non-active displays, does not take place. The active-matrix displays are furthermore very rapid with respect to display formation which is especially advantageous for moved test images.

Liquid-crystal displays can also be used in an advantageous manner which operate on the ferro-electric principle. These cells too have the advantages of being independent of the wavelength of the light used and of providing a rapid display formation. An image which is read-in once remains, even without driving, because the image points in this display have a storage capability. In this way, driving is simple and cross talk between the image points does not occur.

A convenient switchover of the characters generated by the vision testing apparatus is obtained by means of driving the two LCD-displays from a switching unit having a key pad.

The switching unit can be a hard wired circuit or a computer. If a computer is used then any desired character can be generated by means of a simple change of software.

The key pad utilized in the system of the invention is any key pad which is suitable to make a clear selection of the characters to be illustrated by means of the switching unit. The key pad can also be a conventional key pad for a computer.

The intensity of the light source can be varied by the switching unit and, in this way, data concerning the vision acuity of the patient in dependence upon the luminescence and in dependence upon contrast can be obtained.

The vision testing system realized according to the invention can be assembled without mechanically moving parts whereby the system is very robust, free of wear and not subject to disturbances. Furthermore, the system permits a very simple variation in the size of the displayed characters with the characters having any desired form.

In arranging the polarization axes of the polarizers and of the polarization lenses perpendicularly to each other, no clear image separation for the two eyes is obtained when there is a slight inclination in the position of the head of the patient. This image separation is clear for each possible position of the head of the patient when a λ/4 filter is placed in front of the vision testing system and the linearly polarizing polarization lenses of the spectacles are substituted by circularly polarizing polarization spectacles. The λ/4 filters effect a rotary polarization which is independent of the position of the head of the patient.

The color vision of the patient can be evaluated if different switchable color filters are present on the light source or light sources or if different light sources having different colors are provided.

Color vision defects of the patient can be determined by replacing the LCD-display I by a colored liquid-crystal image-generating device, for example, a device as described in U.S. Pat. No. 4,877,309. Furthermore, the test figures can then be shown in color. This is especially desirable for specifying eye lenses.

Additional tests of visual acuity of the patient can be carried out when the test symbols are movable test figures.

With the vision testing system of the invention, the stereo revolving test in the polarization test devices known in the state of the art can be electronically realized for the first time in that the corresponding pixels of the display are simply switched over in LCD II and/or LCD I.

BRIEF DESCRIPTION OF THE DRAWINGS

The invention will now be described with reference to the drawings wherein.

DESCRIPTION OF THE PREFERRED EMBODIMENTS OF THE INVENTION

The self-absorptions of the polarization filters and the liquid-crystal cells shown in FIGS. 1a to 1d are set to zero since they define a constant in all cases considered. In each of the FIGS. 1a to 1d, only one liquid-crystal cell of each display is considered since the same relationships are present for the other displays.

The light emitted by the light source LQ (1) is polarized horizontally by the first color-neutral transparent polarization filter POL I (2). Here, it is assumed that a brightness of 4 H passes through the first polarization filter POL I (2) wherein (n)·(H) is dependent upon the brightness of the light source 1.

Figure 1A:
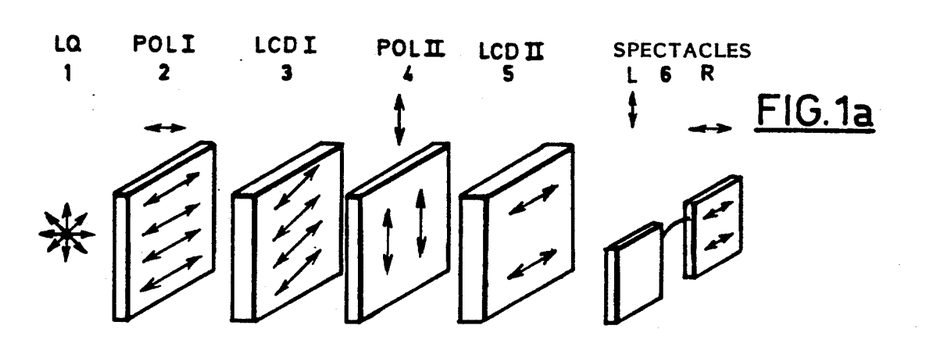
FIGS. 1a to 1d are perspective schematics showing the respective switching states for the four required different visual display types realized with the vision testing system of the invention.

In FIG. 1a, the first liquid-crystal cell LCD I (3) rotates the polarized light incident thereupon by 45°. In this way, only 2 H passes through the second perpendicular polarization filter POL II (4). If the second liquid-crystal cell LCD II (5) rotates the light incident thereupon by 90°, then a brightness of 2 H reaches the right eye R through the polarization spectacles 6 whereas no brightness reaches the left eye L through the polarization spectacles 6. The polarization filters in the polarization spectacles 6 are then so aligned that the polarization filter in front of the left eye L has a vertical polarization axis and the polarization filter in front of the right eye R has a horizontal polarization axis.

The two liquid-crystal cells LCD I and LCD II are arranged one behind the other so that the light of the light source LQ1 passes through both cells before it reaches the spectacles 6 of the viewer. Whether this light can be seen through the right or left spectacle lens is dependent upon the direction of oscillation of the light leaving the second liquid-crystal cell LCD II because the polarization direction of the polarization filters of the left and right spectacle lenses are orientated perpendicularly to each other. In FIGS. 1a to 1d, the left spectacle lens L has a vertical polarization and the right spectacle lens R has a horizontal polarization.

Figure 1B:
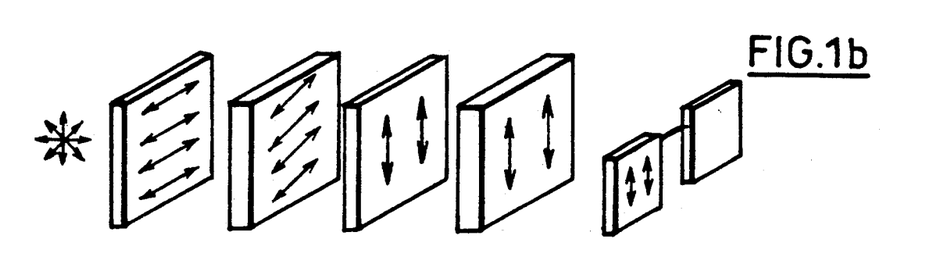

In contrast to FIG. 1a, the second liquid-crystal cell LCD II (5) in FIG. 1b rotates the light incident thereupon by 0° so that no brightness reaches the right eye R; whereas a brightness of 2 H reaches the left eye L.

Figure 1C:
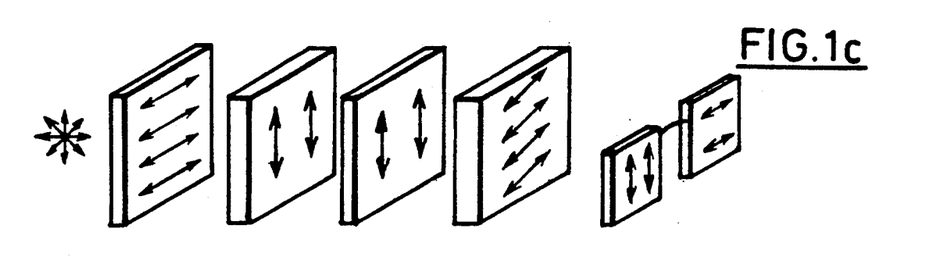

In FIG. 1c, the first liquid-crystal cell LCD I (3) rotates the light incident thereupon by 90° and the second liquid-crystal cell LCD II (5) rotates the light incident thereupon by 45°. Then, a brightness of 2 H reaches both eyes (L, R).

Figure 1D:
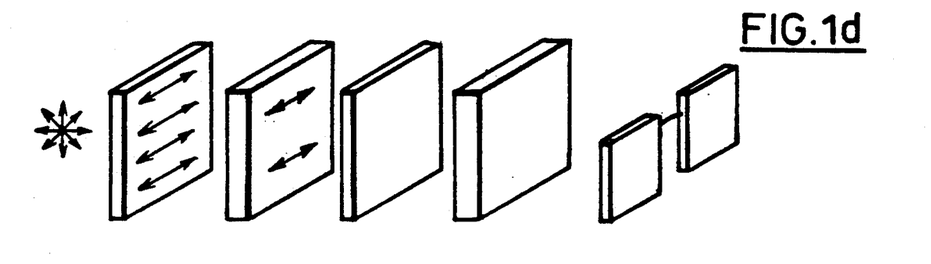

If, in contrast, as shown in FIG. 1d, the first liquid-crystal cell LCD I (3) rotates the light falling thereupon by 0° then no brightness reaches the two eyes (L, R).

Figure 2A:
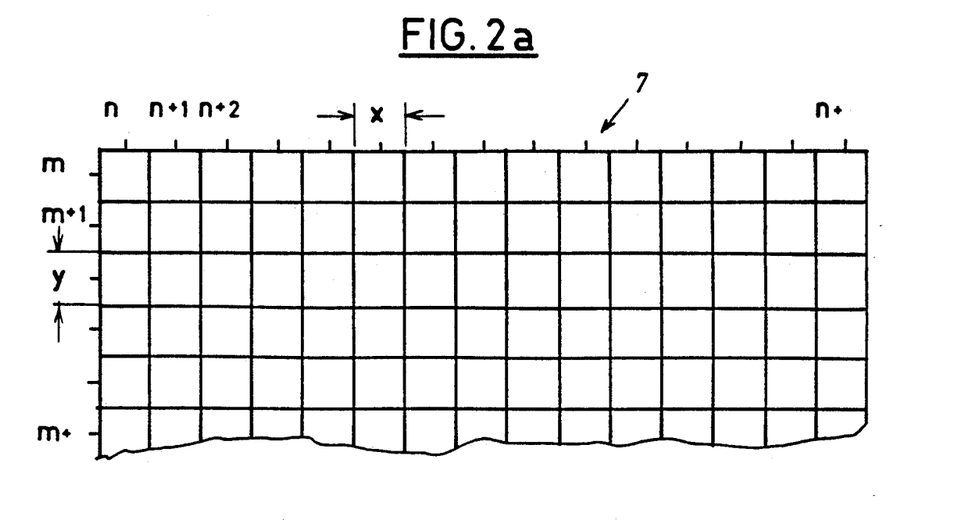
FIG. 2a shows a portion of a LCD-display assembled from a plurality of liquid-crystal cells.

If a plurality of liquid-crystal cells 3 are now placed one next to the other, then an LCD-display 7 as shown in FIG. 2a is obtained. A second LCD-display corresponding to the LCD-display 7 is obtained by placing a plurality of liquid-crystal cells 5 one next to the other. In FIG. 2a, (x) identifies the horizontal expansion of n+cells and (y) identifies the vertical expansion of m+cells of the liquid-crystal cell of the display 7.

With the display 7, figures and characters can be illustrated in that the individual liquid-crystal cells are driven as will now be explained with reference to FIGS. 1a to 1d.

The individually drivable liquid-crystal cells must satisfy certain conditions so that the two displays needed for carrying out the invention are adapted to each other.

If for the first display, the horizontally arranged liquid-crystal cells are identified by n (1), n (1)+1, ..., n (1)+q (1) and the vertically arranged liquid-crystal cells are identified by m (1), m (1)+1, ..., m (1)+k (1), then the number of liquid-crystal cells of the second display n (2), n (2)+1, ..., n (2)+q (2); m (2), m (2)+1, ..., m (2)+k (2) must satisfy the following conditions:

$$\Sigma n(1)+q(1)=z\neq\Sigma n(2)+q(2) \text{ with } z\epsilon N\neq 0$$
$$n(1)+q(1)>Z$$

or $$\Sigma n(1)+q(1)=1/z^*\Sigma n(2)+q(2) \text{ with } z\epsilon N\neq 0$$
$$n(1)+q(1)>Z$$

that is, the number of liquid-crystal cells of the second display in horizontal or vertical direction may deviate from each other by a multiple of a whole number without blurred margins occurring for the characters Which must be displayed. In the above equations, z is the number of liquid-crystal cells and $z\epsilon N$ means that z is an element of the whole number (1, 2, 3, ... 1000, ... ).

Resolution losses are however obtained with the display of characters except when $z=1$.

During assembly, the liquid-crystal cells of the two displays must be arranged one behind the other so that the liquid-crystal cells of the first display, individually or in combination, fall precisely on one or more liquid-crystal cells of the second display so that distinguishable characters can be displayed.

Figure 2B:
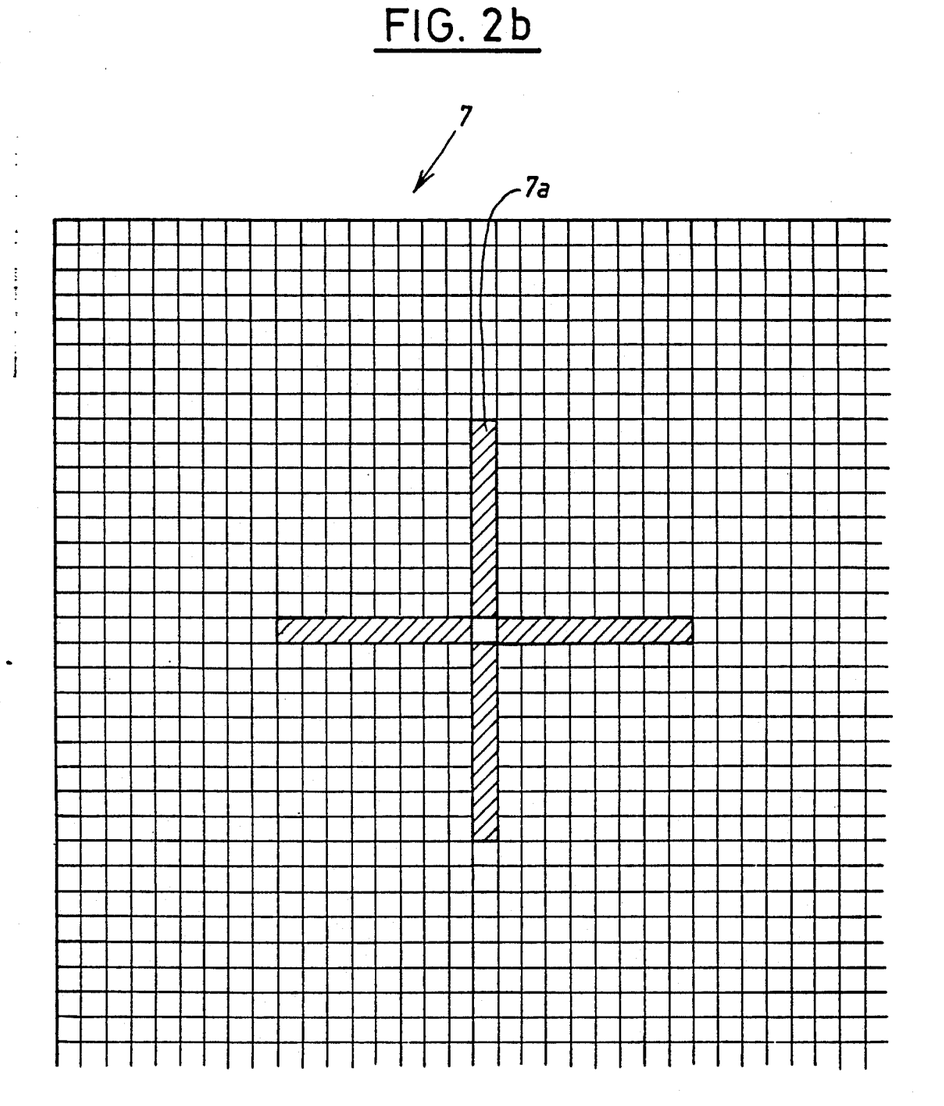
FIG. 2b shows a complete LCD-display of the kind shown in FIG. 2a displaying a test figure for determining monocular predominance.

FIG. 2b shows a complete LCD-display corresponding to the display of FIG. 2a and showing a test figure for determining monocular predominance.

FIGS. 3 to 6 show different embodiments of the vision testing system of the invention and will now be described.

The corresponding test figures must be presented under different conditions for testing the different binocular and monocular sight functions.

Figure 3:
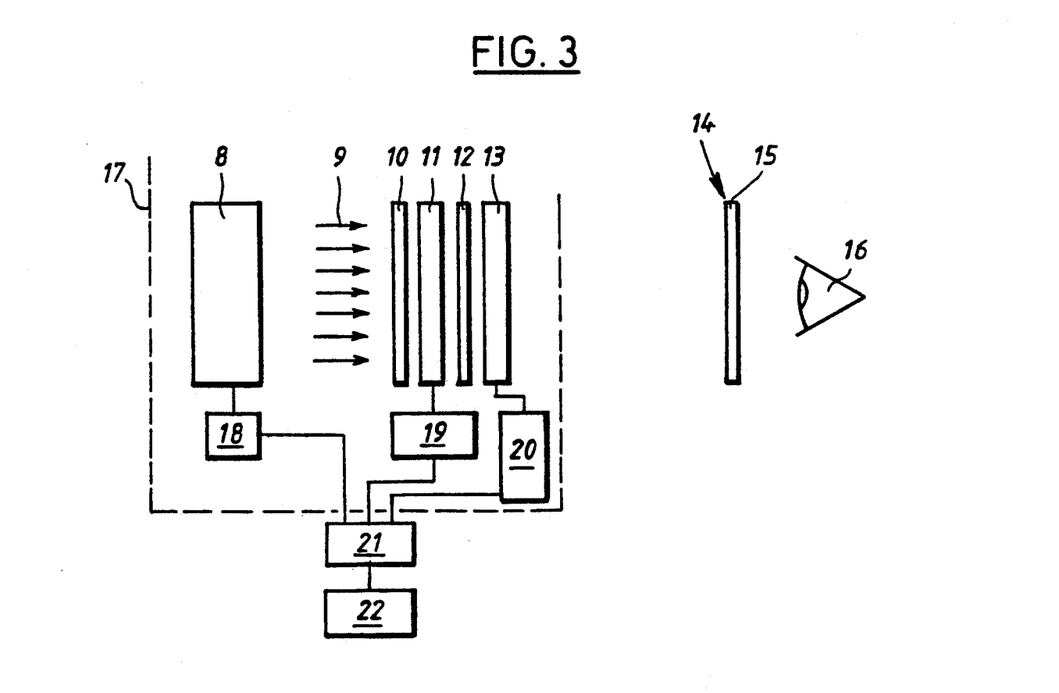
FIG. 3 is a schematic of the vision testing system according to a preferred embodiment of the invention.

For testing the binocular sight functions, spectacles 14 are placed on the patient having a polarization lens 15 for each eye 16. The polarization lenses 15 are seated in the spectacles 14 so that the polarization axes of both polarization lenses 15 are as perpendicular as possible to each other.

For carrying out the test of the binocular vision functions, the vision testing system 17 must provide at least the following display configurations:

(1) portions of a test figure appear dark for one eye in front of a bright background;

(2) portions of a test figure appear bright for one eye in front of a dark background;

(3) different portions of a test figure appear dark for both eyes in front of a bright background; and, (4) different portions of a test figure appear bright for both eyes in front of a dark background.

For display configurations (1) and (2), the portions of the test figure visible for the one eye are invisible to the other eye.

The testing of monocular sight functions can also be undertaken without the polarization spectacles 14 which requires that at least the following conditions are realized:

(5) a test figure appears for both eyes dark against a bright background; and, (6) a test figure appears bright for both eyes against a dark background.

When testing the acuity of color vision, it is furthermore necessary that the following conditions be realized:

(7) portions of a test figure appear with different colors for both eyes in front of a background having another color;

(8a) a test figure appears in color for both eyes in front of a bright background; and, (8b) a test figure appears in color for both eyes in front of a dark background.

In order to realize conditions 1 to 4, the vision testing system 17 of the invention must be configured as described below. A light source 8 illuminates with its light a first color-neutral transparent polarization filter 10. The light passing through the first polarization filter 10 penetrates a first LCD-display 11 and illuminates a second color-neutral polarization filter 12. The light passing through the second polarization filter 12 penetrates a second LCD-display 13 whereafter the light leaves the vision testing device 17.

A color-neutral transparent polarization lens 15 is disposed forward of each eye 16 of the patient to be tested. Each of the LCD-displays (11, 13) is connected to its own drive circuit (19, 20). The two drive circuits (19, 20) are connected to a switching unit 21. This switching unit 21 is operated via a key pad 22 and controls the two drive circuits (19, 20). The switching unit 21 and the key pad 22 can be disposed within or on the vision testing device 17, or a switchover of the test figures in the vision testing device 17 can be effected via remote control configured in accordance with the state of the art, for example, by means of a cable connection, infrared connection or ultrasound connection.

The vision acuity of the patient can also be tested in dependence upon the luminescence and upon the contrast. This is done in that the light source 8 is additionally influenced with respect to its intensity by means of the light source drive circuit 18 driven by the switching unit 21 connected to the light source 8.

The monocular and binocular (without separation of the visual impressions of the right and left eye) vision functions can also be tested since the conditions 5 and 6 can also be realized with the vision testing device 17. The patient can then leave the polarization spectacles 14 on or remove the same.

If a check of the acuity of color vision of the patient is to take place, then the vision testing device must be able to display test figures and also parts thereof in color. Vision testing systems according to the invention capable of performing the above will now be described with reference to FIGS. 4a, 5 and 6.

Figure 4A:
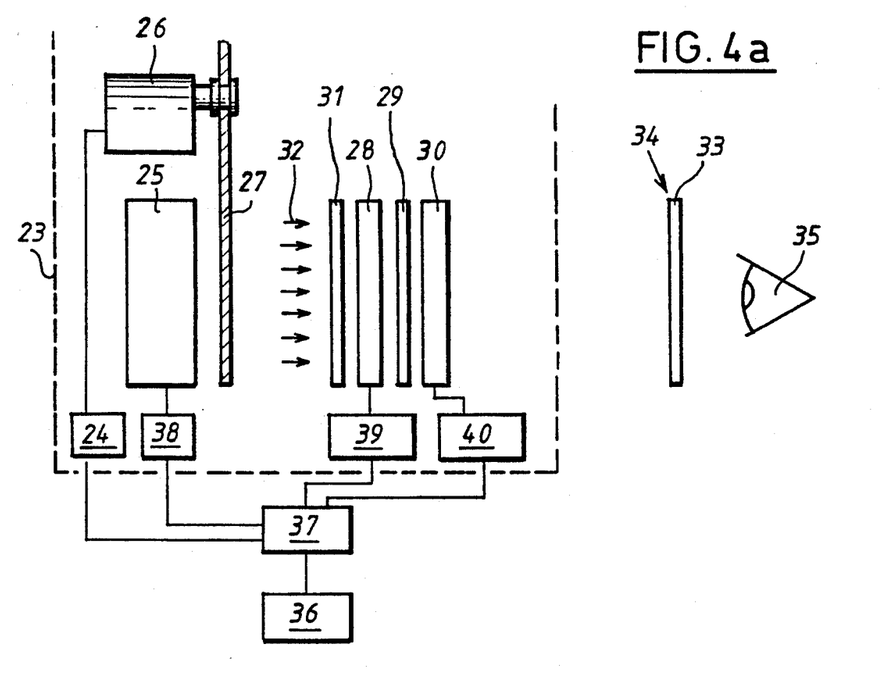
FIG. 4a is a schematic of an embodiment of the vision testing system of the invention equipped with a color filter.

In FIG. 4a, the simplest configuration of one such color vision testing device 23 is schematically shown. The vision testing device 23 includes two polarization filters (29, 31) and two LCD-displays (28, 30). The two LCD-displays (28, 30) are connected via their drive circuits (39, 40) to the switching unit 37 to which a key pad 36 is connected.

In addition to the elements of the vision testing device 17 already described with respect to FIG. 3, the vision testing device 23 includes a color-filter disc 27 which can be rotated by a motor 26. The input takes place via the key pad 36 to the switching unit 37 so that a specific color filter, for example, red (r), yellow (g), blue (b) and neutral (n) (as shown in FIG. 4b) is disposed forward of the light source 25.

The instantaneous position of the color-filter disc 27 is checked in the switching unit 37 and when the color-filter disc 27 is not in the desired position, the motor drive 24 of the motor 26 of the color-filter disc is driven to rotate the color-filter disc 27 into the desired position. In FIG. 4b, the color-filter disc 27 is shown in a view. The region of the first polarization filter 31 is also shown.

Figure 4B:
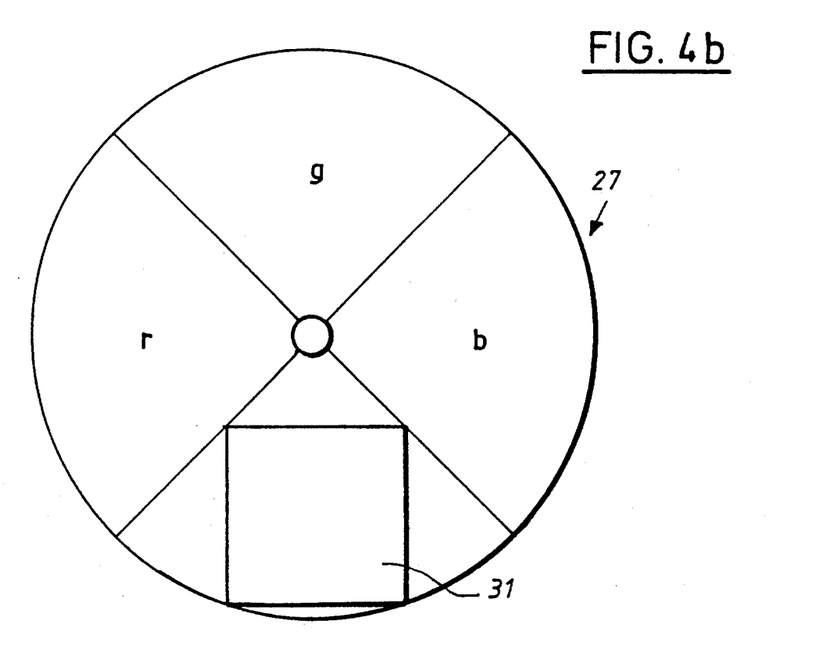
FIG. 4b is a front elevation view of the color filter.

Only the color of the entire illuminating light 32 can be changed with the color-filter disc 27 shown in FIGS. 4a and 4b. A color display with different colors is not possible. For this reason, in FIG. 5, the color-filter disc 27 having motor 26 and motor drive 24 is replaced by a color-LCD 44 having a drive circuit 54 with the drive circuit 54 being connected to the switching unit 56. A color liquid-crystal image-generating unit is shown, for example, in U.S. Pat. No. 4,877,309 incorporated herein by reference.

Figure 5:
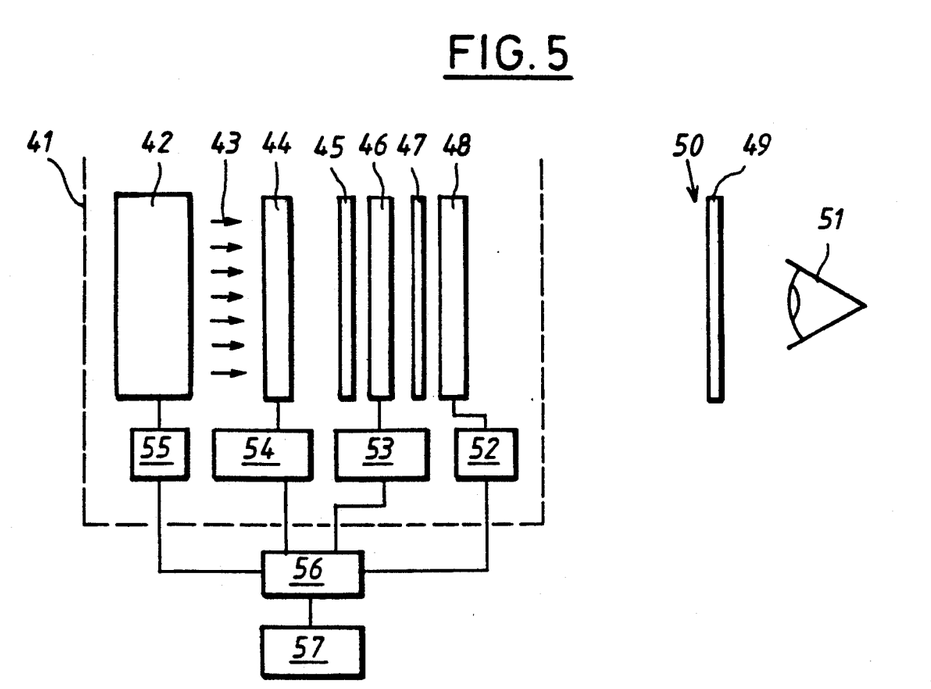
FIG. 5 is a schematic of still another embodiment of the vision testing system of the invention; and, FIG. 6 is a schematic of a further embodiment of the vision testing system of the invention.

The light 43 of light source 42 first passes through the color-LCD 44. There, tile light is changed in its color in the desired manner. Only then are the test figures generated by the two polarization filters (45, 47) and the two LCD-displays (46, 48). The light source 42 can be influenced in its intensity by the switching unit 56 via the light source drive circuit 55. The two LCD-displays (46, 48) are connected via their drive circuits (53, 52) to the switching unit 56.

The eyes 51 of the patient can then see a color image through the polarization spectacles 50 having the polarization filters 49.

The resolution of this color-LCD 44 has to be adapted to the resolution of the two other LCDs (46, 48) in accordance with the above description with respect to resolution.

With a vision testing device 41 configured in this manner, a colored configuration of the displayed test figure as well as a display of movable test figures is possible.

Figure 6:
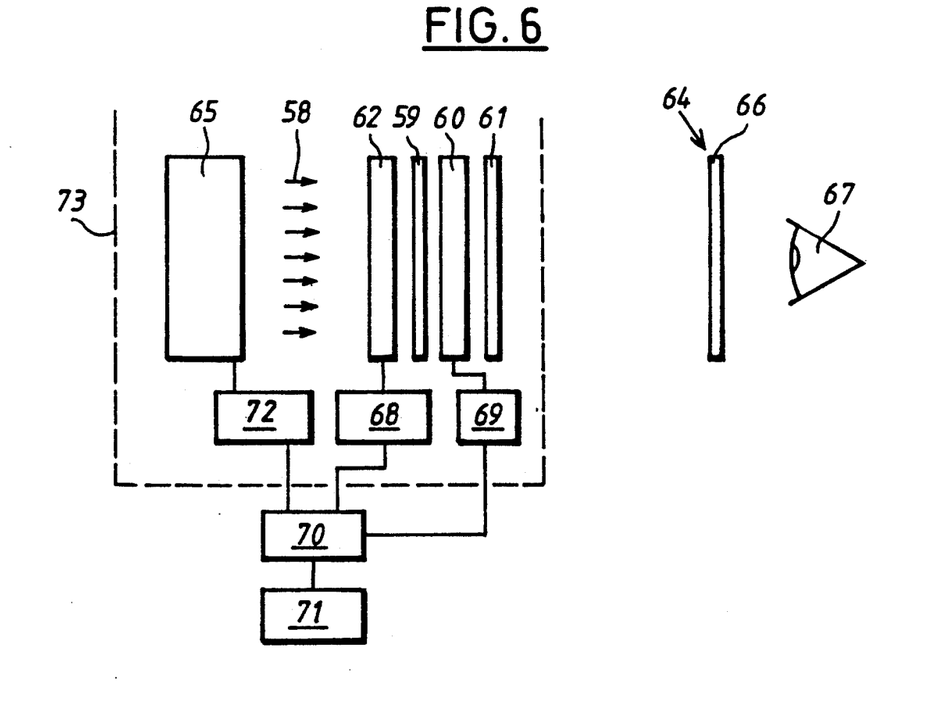

A simplification of the configuration of the vision testing device 41 of FIG. 5 can be obtained when the first polarization filter POL I (7) and the first LCD-display (8) with drive circuit 11 are substituted entirely by a color-LCD 62 having drive circuit 68.

The light 58 of light source 65 then first penetrates the color-LCD 62. The light exiting the Color-LCD 62 is then rotated with the desired test figure by means of the following polarization filter 59 and the LCD-display 60 in the desired manner. A λ/4 filter 61 is disposed downstream of the LCD-display 60 which polarizes the light passing therethrough either circularly left or circularly right.

In the spectacles 64 forward of the eye 67 of the patient, λ/4 filters 66 are placed on the polarization filter so that the conditions 1 to 4, 5 and 6 as well as the conditions 7, 8a and 8b for testing the visual acuity of the patient can be realized.

The use of the λ/4 filters on the polarization filters (61, 64) affords the advantage that even for an inclined position of the head of the patient, the eyes of the patient always see what they are intended to see.

The vision testing device according to the invention is characterized by its compact, trouble-free configuration and permits a check of monocular and binocular visual functions as well as a check of the color acuity of the patient.

The described polarization spectacles can also be configured as insertable sets which can be mounted on conventional spectacles of the patient for checking the visual functions.

It is understood that the foregoing description is that of the preferred embodiments of the invention and that various changes and modifications may be made thereto without departing from the spirit and scope of the invention as defined in the appended claims.

What is claimed is:

1. A vision testing system for testing the sight functions of a patient, the system comprising:
   polarization spectacles having first and second polarization lenses for placement in front of the first and second eyes of the patient, respectively;
   said first polarization lens defining a first polarization axis and said second polarization lens defining a second polarization axis perpendicularly to said first polarization axis; and,
   a vision testing apparatus including:
   a light source for radiating light defining a light axis;
   a first LCD-display mounted on said light axis downstream of said light source and including a plurality of first individually drivable liquid-crystal cells;
   a second LCD-display mounted on said light axis downstream of said first LCD-display and including a plurality of second individually drivable liquid-crystal cells;
   the cells of each of said displays being aligned with respect to each other and being adapted to each other with respect to their size;
   a color-neutral transparent first polarizer mounted on said light axis between said light source and said first LCD-display;
   a color-neutral transparent second polarizer mounted on said light axis between said first and second LCD-displays;
   said first polarizer defining a third polarization axis and said second polarizer defining a fourth polarization axis; said third and fourth polarization axes having different directions relative to each other;
   a first drive circuit for individually driving said cells of said first LCD-display;
   a second drive circuit for individually driving said cells of said second LCD-display;
   switching means connected to said first and second drive circuits for controlling both of said first and second drive circuits; and,
   key pad means for issuing commands to said switching means for driving said first and second drive circuits to, in turn, individually drive the cells of said LCD-displays.

2. The vision testing system of claim 1, said vision testing apparatus further comprising an additional drive circuit connected to said switching means for changing the intensity of the light of said light source.

3. The vision testing system of claim 2, said first and second polarization axes, and said third polarization axis being arranged in two mutually parallel planes; and, said first and second polarization axes, and said fourth polarization axis likewise being arranged in two mutually parallel planes.

4. The vision testing system of claim 2, said third and fourth polarization axes being perpendicular to each other; said first and second polarization axes, and said third polarization axis being arranged in two mutually parallel planes; and, said first and second polarization axes, and said fourth polarization axis likewise being arranged in two mutually parallel planes.

5. The vision testing system of claim 1, said vision testing apparatus further comprising: a first λ/4 filter mounted forward of said second LCD-display and a second λ/4 filter mounted forward of said first and second polarization lenses.

6. The vision testing system of claim 1, said vision testing apparatus further comprising: color means for changing the color of the light emitted by said light source; and drive means connected to said switching means for driving said color means for changing said color.

7. The vision testing system of claim 1, said vision testing apparatus further comprising: a color liquid-crystal image generating device mounted forward of said first LCD-display.

8. The vision testing system of claim 1, wherein said switching means and said key pad means are adapted to produce selectable movable test figures on said LCD-displays.

9. The vision testing system of claim 1, wherein said first LCD-display is configured as a color liquid-crystal image generating device.

* * * * *

UNITED STATES PATENT AND TRADEMARK OFFICE
CERTIFICATE OF CORRECTION

PATENT NO. : 5,331,358
DATED      : July 19, 1994
INVENTOR(S) : Hermann Schürle, Wolfgang Grimm and Hartmut Mennicke It is certified that error appears in the above-identified patent and that said Letters Patent is hereby corrected as shown below:

In column 2, line 34: delete "Wavelength" and substitute -- wavelength -- therefor.

In column 3, line 65: delete "self-absorptions" and substitute -- self-absorption -- therefor.

In column 4, line 45: between "0°" and "then", insert -- , --.

In column 5, line 12: delete "Which" and substitute -- which -- therefor.

In column 6, line 66: after "a" insert -- front --.

In column 7, line 12: delete "tile" and substitute -- the -- therefor.

In column 7, line 38: delete "Color-LCD 62" and substitute -- color-LCD 62 -- therefor.

Signed and Sealed this

Twenty-seventh Day of September, 1994

Attest:

BRUCE LEHMAN

*Attesting Officer*          *Commissioner of Patents and Trademarks*